United States Patent [19]

Landis

[11] Patent Number: 4,945,573
[45] Date of Patent: Aug. 7, 1990

[54] VISOR AND SHIELD ATTACHED TO EYEGLASSES

[76] Inventor: Timothy J. Landis, 2006 McLaren Dr., Roseville, Calif. 95661-4945

[21] Appl. No.: 214,437

[22] Filed: Jul. 1, 1988

[51] Int. Cl.$^5$ .............................................. A61F 9/04
[52] U.S. Cl. .............................................. 2/9; 2/10; 2/13; 128/863; 351/158
[58] Field of Search ...................... 2/13, 12, 9, 10, 206, 2/171, 173, 427, 199; 351/158, 44, 47; 128/863, 857

[56] References Cited

U.S. PATENT DOCUMENTS

| | | | |
|---|---|---|---|
| 1,199,529 | 9/1916 | Collman | 128/139 |
| 1,202,513 | 10/1916 | Gudger | 2/10 |
| 1,673,859 | 6/1928 | Wittcoff | 2/10 X |
| 2,541,242 | 2/1951 | Grove | 2/13 |
| 2,638,593 | 5/1953 | Eloranta | 2/12 |
| 2,724,834 | 11/1955 | Henderson | 2/13 |
| 3,089,145 | 5/1963 | Kiefer | 2/13 X |
| 3,183,523 | 5/1965 | Harrison | 2/13 |
| 3,458,866 | 8/1969 | De Man | 2/13 X |
| 3,991,753 | 11/1976 | Viesca | 2/9 X |
| 4,543,667 | 10/1985 | Garbutt | 2/13 |
| 4,625,341 | 12/1986 | Broersma | 2/9 X |
| 4,701,965 | 10/1987 | Landis | 2/9 X |
| 4,768,231 | 9/1988 | Schrack | 2/13 |
| 4,850,049 | 7/1989 | Landis et al. | 2/10 |

FOREIGN PATENT DOCUMENTS

| | | | |
|---|---|---|---|
| 1174669 | 11/1958 | France | 2/10 |
| 0074877 | 3/1929 | Sweden | 128/139 |
| 0556664 | 12/1974 | Switzerland | 128/139 |

Primary Examiner—Peter Nerbun
Attorney, Agent, or Firm—Julian Caplan

[57] ABSTRACT

A mask to protect physicians, dentists and technicians from spatter from patients afflicted with various diseases (including A.I.D.S.) is assembled from two parts, which may be shipped and stored flat. The visor is formed of a flat piece of sheet rubber formed with transverse slits so that the visor may be attached to ordinary eyeglasses. The shape of the visor provides a curved, forward extending bill. Slits are formed near the outer edge of the visor. A transparent shield has dovetail projections on its upper edge which snap through the slits. Other cooperating fastening means may be used to assemble the visor and shield and also to hold the visor on eyeglasses. The shield is supported by the visor and hangs down to about the chin, protecting the eyes, nose and mouth.

3 Claims, 1 Drawing Sheet

U.S. Patent
Aug. 7, 1990
4,945,573
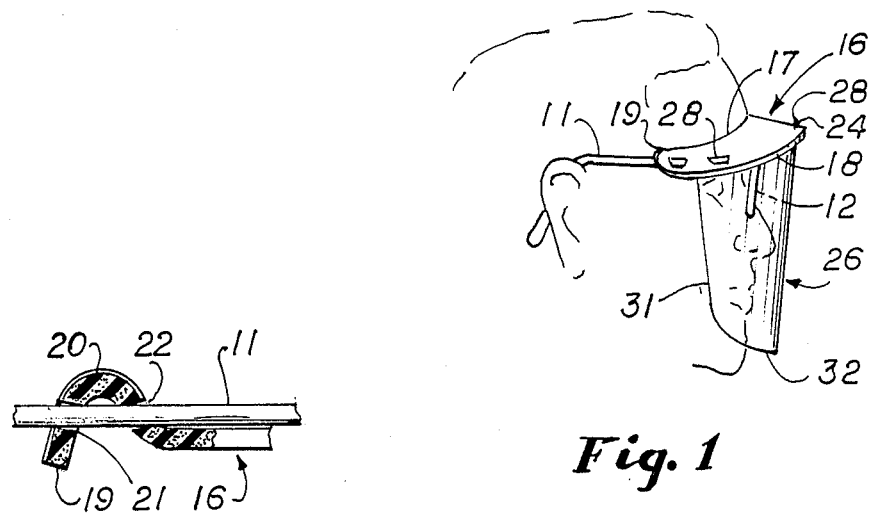
Fig. 1
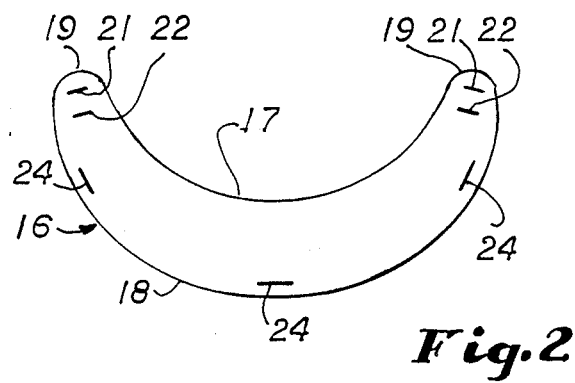
Fig. 4
Fig. 2
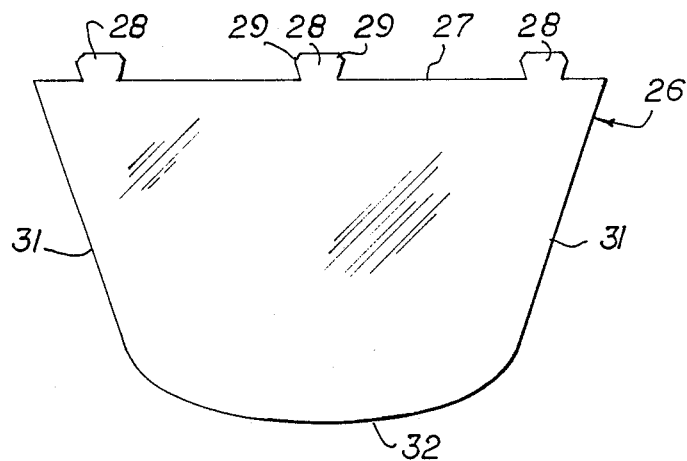
Fig. 3

VISOR AND SHIELD ATTACHED TO EYEGLASSES

CROSS-REFERENCE TO RELATED APPLICATIONS

Reference is made to Applicant's U.S. Pat. No. 4,701,965 and co-pending application Ser. No. 194,150, filed May 16, 1988, entitled PROTECTIVE SHIELD AND VISOR SUPPORTING SAME.

BACKGROUND OF THE INVENTION

1. Field of the Invention

This invention relates to a new and improved mask for use by dentists, surgeons and others to avoid contamination with germs and viruses of their patients and customers. A feature of the invention is the fact that the visor is made of a flexible material and shaped so that the temples of the eyeglasses worn by the user may be inserted through transverse slits near the ends of the visor. When eyeglasses are worn, the visor is so positioned that it projects forwardly of the forehead of the wearer above the level of the eyeglasses. A transparent plastic shield of sheet plastic attaches to the visor and extends down below the level of the mouth of the wearer and around the sides of the head, thus providing superior frontal and lateral protection from splashing and spattering with bodily fluids of the patient or customer.

2. Description of Related Art

Surgical masks of gauze and paper have been used to prevent intercontamination of doctor and patient. However, wearing such masks is hot and uncomfortable and, frequently, frightening to patients. Putting on the mask and removing same are time-consuming and sometimes difficult. Breath condenses within the mask and hence the latter becomes saturated with moisture and thereby fails to be an effective barrier to viruses and bacteria.

Further, conventional masks cause the wearer to re-inhale exhaled breath, causing the $CO_2$ content of the blood to rise. The result of this may be increased heart and respiration rates and higher body temperatures and perspiration.

U.S. Pat. No. 4,701,965 illustrates a visor-type mask for dentists and dental technicians which is commercially successful. This reference shows a visor which attaches to the head and a transparent shield supported thereby. In the present invention, the visor is intended for use by persons wearing eyeglasses. The temple bars of the eyeglasses are inserted through slits on the ends of the visor so that the eyeglasses support the visor and the visor, in turn, supports the transparent plastic shield.

The attachment of the transparent shield to the visor is simplified.

A feature of the invention is the fact that the eyeglasses support the weight of the device and, since the user is accustomed to the weight of eyeglasses, localized pressure on the head and an unusual weight load are not sensed.

Another feature of the invention is the fact that its construction is somewhat less expensive than previous masks of applicant.

Other references are discussed in U.S. Pat. No. 4,701,965 and additional references were cited by the U.S. Patent and Trademark Office prior to the issuance of said patent.

SUMMARY OF THE INVENTION

The present invention consists of two main pieces. A visor of a sheet of rubber or rubberlike material is initially flat and bendable. A pair of slits is formed transversely adjacent each end of the visor and these receive the temple bar of eyeglasses so that the visor is attached to the eyeglasses. The visor may be attached to the glasses in other ways.

When installed on the eyeglasses and the eyeglasses are worn in normal fashion, the visor fits around the forehead and extends downward-forward away from the head in a peaked bill which is upward-convex. Contact of the visor with the forehead is substantially continuous all around so that contaminants are not likely to fall inside the shield by slipping through a gap between the visor and the head.

A removable, transparent, flexible plastic shield is suspended from the front edge of the visor using slits formed adjacent the outer margin. In a preferred form, the visor has dovetail projections along its upper edge which slip into the slits along the outer edge of the visor and lock therein. Alternatively, the shield may be attached to the visor by snaps, adhesive, Velcro materials, and other means. The shield curves outward and extends downward so as to protect the eyes, nose and mouth of the wearer from contamination from the front or sides.

With the eyeglasses worn and the shield in place, the latter is supported and protects the eyes, nose and mouth from contamination by blood, body fluids and the like of a patient. Because the shield is forward of the mouth and nose, air may flow up from below the face and from the sides so that carbon dioxide buildup from rebreathing expelled air, fogging of the eyeglass lenses of the wearer, and saturation of the mask by spattering or splashing with bodily fluids do not occur.

The visor and shield are inexpensively fabricated by stamping from flat sheets of material, thus avoiding more expensive techniques such as injection molding and other expensive fabricating techniques.

Other objects of the present invention will become apparent upon reading the following specification and referring to the accompanying drawings in which similar characters of reference represent corresponding parts in each of the several views.

IN THE DRAWINGS

FIG. 1 is a perspective view showing the mask of the present invention installed on eyeglasses worn on the head of the user.

FIG. 2 is an enlarged plan view of the visor.

FIG. 3 is an enlarged plan view of the shield.

FIG. 4 is a further enlarged fragmentary view, partly broken away in the section showing attachment of an end of the visor to a temple bar of eyeglasses.

DESCRIPTION OF PREFERRED EMBODIMENT

The present invention may be used in combination with any sort of conventional eyeglasses of the type having sidepieces 11 (i.e., temple bars) attached in any suitable manner to portions which support lenses 12 for either eye.

Visor 16 is preferably of sheet rubber or sheet rubber-like material which is light in weight and bendable. As best shown in FIG. 4, one or both surfaces of the rubber portion may be covered with fabric 20 or an ornamental coating. The fabric also confines the amount of curving or other distortion of the rubber. The inner edge 17 is curved to conform to the forehead of the wearer and the outer edge 18 is likewise curved, preferably having a slightly greater radius of curvature than surface 17. Ends 19 are rounded. At each end 19 is an outer and an inner transverse slit 21, 22. As shown in FIG. 4, the sidepiece 11 is pushed first through the outer slit 22 from the under side of the visor and then through the inner slit 21. Because the visor 16 is of a flexible material, the insertion of the sidepiece 11 is formed with very little difficulty and the soft, flexible nature of the material makes it comfortable to wear. Other means may be used to attach the visor to the eyeglasses. The visor 16 has a curved, peaked shape which extends forward and slants down and projects forwardly and downwardly beyond the lenses 12 in a bill. Additional slits 24, here shown as three in number, are formed spaced along the outer edge 18.

Shield 26 is formed of a thin sheet of transparent plastic. Upper edge 27 has integral upward extending projections 28 which are generally dovetail shaped with the corners 29 truncated. The length of slits 24 is such that when the projections 28 are pushed therethrough (the truncated corners 29 facilitating insertion), the projections 28 are not readily unintentionally removable. Side edges 31 are downwardly converging and the bottom edge 32 is preferably curved.

Thus both the visor 16 and shield 26 may be stamped out of flat sheet material by inexpensive fabricating steps.

When worn, a shown in FIG. 1, the shield 26 protects the eyes, nose and mouth of the wearer, and the edges 31 curve around the side of the face so that the wearer is protected not only from material from the front but also the sides.

It will be understood that the shield 26 may be attached to the visor 16 by means other than the projections 28 and slits 24 as, for example, by snaps, adhesive, Velcro materials, or other means. Additionally, the visor 16 may be attached to the eyeglasses by other means such as clips, clamps, Velcro materials and the like.

What is claimed is:

1. A face mask comprising an integral visor, said visor being formed of an initially flat resilient, flexible sheet of rubber-like material bent to assume a visor shape when said visor is attached to the eyeglasses of a user, means for attaching said visor to eyeglasses worn by the user, said visor being formed with an inner edge shaped to fit against the forehead of the user and a curved outer edge, said visor being substantially horizontal when in position of use, said visor being formed with a plurality of spaced slits through said visor spaced along said outer edge, and a removable shield formed of a sheet of flexible plastic transparent over at least a substantial portion of its area, said shield having an upper edge formed with projections, said shield and said projections being formed together as a one piece structure, said projections dimensioned to be resiliently forced through said slits and preventing unintentional detachment of said shield from said visor, so that said shield is supported by said visor extending substantially vertically, said shield being shaped and dimensioned to extend down and around the face of the user to protect the eyes, nose and mouth from contamination.

2. A mask according to claim 1 in which said projections are dovetail, having a maximum width greater than the lengths of said slits when said visor is unstressed.

3. A mask according to claim 1 in which said rubber-like material is covered on at least one surface with fabric.

* * * * *